(12) United States Patent
Tanaka et al.

(10) Patent No.: US 7,189,968 B2
(45) Date of Patent: Mar. 13, 2007

(54) SAMPLE MEASUREMENT METHOD AND MEASUREMENT SAMPLE BASE MATERIAL

(75) Inventors: Yoshitomo Tanaka, Tokyo (JP);
Masaki Takahashi, Tokyo (JP);
Tomoyuki Oike, Tokyo (JP)

(73) Assignee: TDK Corporation, Tokyo (JP)

( * ) Notice: Subject to any disclaimer, the term of this patent is extended or adjusted under 35 U.S.C. 154(b) by 182 days.

(21) Appl. No.: 10/926,951

(22) Filed: Aug. 27, 2004

(65) Prior Publication Data
US 2005/0082478 A1 Apr. 21, 2005

(30) Foreign Application Priority Data
Aug. 29, 2003 (JP) ............................ P2003-308058

(51) Int. Cl.
*G01N 1/28* (2006.01)
*H01J 37/20* (2006.01)
(52) U.S. Cl. ...................... 250/307; 250/304; 250/311; 250/310
(58) Field of Classification Search ..................... None
See application file for complete search history.

(56) References Cited

U.S. PATENT DOCUMENTS 5,525,806 A * 6/1996 Iwasaki et al. ............. 250/307
6,395,347 B1 * 5/2002 Adachi et al. ............... 250/311
6,538,254 B1 * 3/2003 Tomimatsu et al. ..... 250/442.11

FOREIGN PATENT DOCUMENTS

JP     A 5-231997     9/1993
JP     A 10-19751     1/1998

OTHER PUBLICATIONS

"Device Analysis Guidebook"; Edited by Japan Society for Analytical Chemistry, Maruzen Co. Ltd.,; Jul. 10, 1996; pp. 138-142 w/transl.
"Transmission Electron Microscope"; Edited by Surface Science Society of Japan, Maruzen Co. Ltd.,; Apr. 15, 2001; pp. 33-42 w/transl.

* cited by examiner

*Primary Examiner*—Jack I. Berman
(74) *Attorney, Agent, or Firm*—Oliff & Berridge, PLC

(57) ABSTRACT

A sample measurement method is a sample measurement method by an electron microscope and includes the film formation step of forming a sample on a projection on the major surface of a substrate, the electron beam irradiation step of irradiating the sample with an electron beam from a side of the projection, and the measurement step of detecting an electron beam which is generated or reflected from or has passed through the sample irradiated with the electron beam. Since the sample is formed on the projection on the major surface of the substrate, the sample on the projection can be formed as a thin film. For this reason, sample measurement can be executed only by irradiating the sample from a side of the projection.

12 Claims, 12 Drawing Sheets

Fig.8
(a)
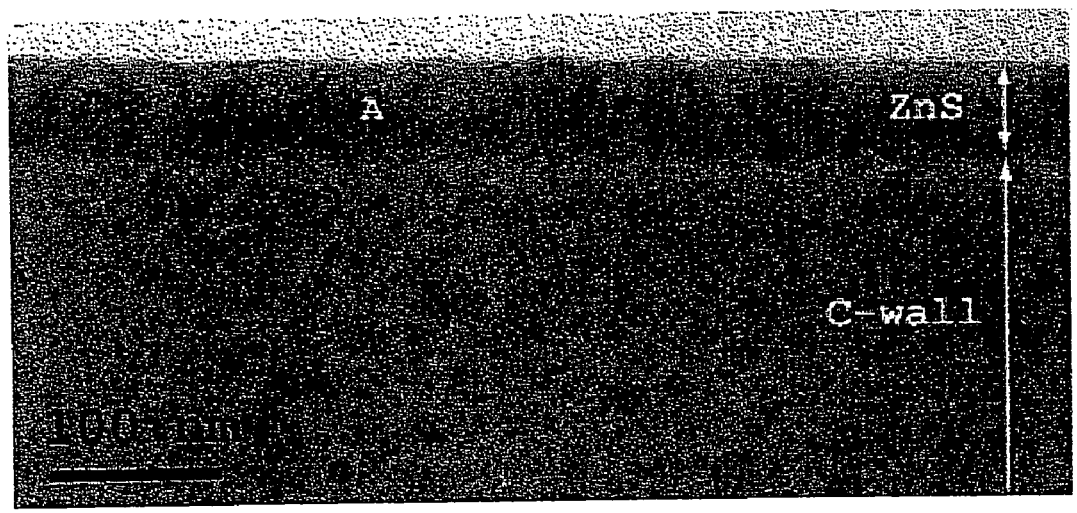
(b)
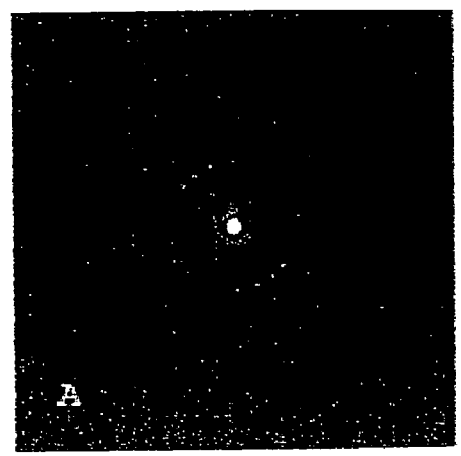

Fig.9
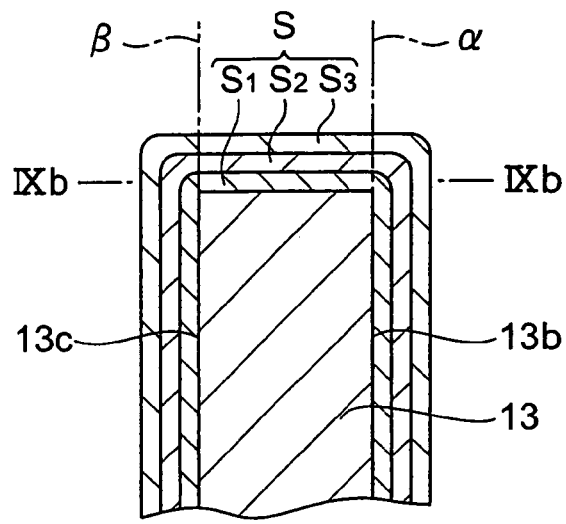
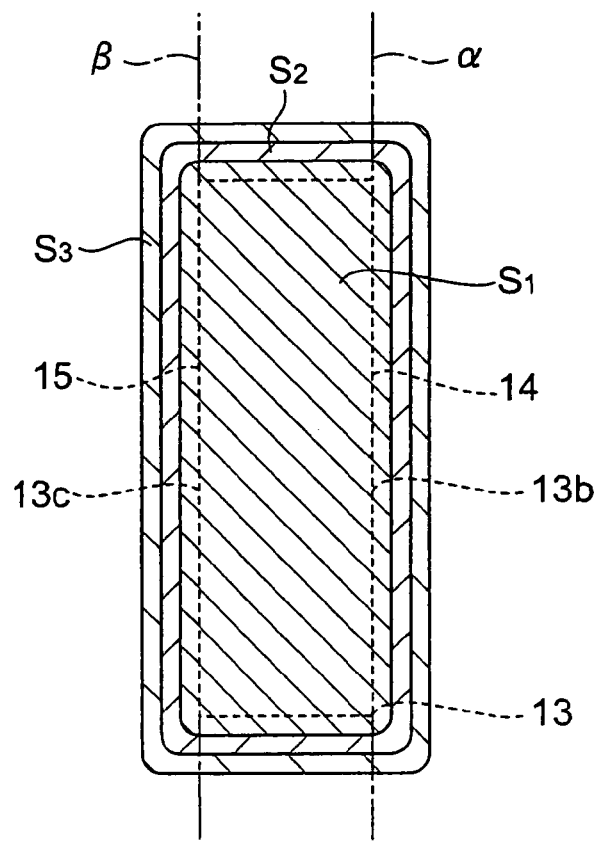

SAMPLE MEASUREMENT METHOD AND MEASUREMENT SAMPLE BASE MATERIAL

BACKGROUND OF THE INVENTION

1. Field of the Invention

The present invention relates to a sample measurement method and measurement sample base material and, more particularly, to a sample measurement method by an electron microscope, and more specifically, by a transmission electron microscope and a measurement sample base material.

2. Related Background Art

Fluorescent X-ray analysis is widely used for thickness measurement or composition analysis of thin films (reference D1). X-ray diffraction analysis or electron diffraction analysis is known as a method of evaluating the crystal structure of a thin film.

To measure the thickness of a thin film by fluorescent X-ray analysis, it is necessary to accurately know the density of the thin film. However, accurate measurement is difficult because the actual density is often different from the reference value. When the thin film as a sample to be measured is a multilayered film, the X-ray dose from each layer must accurately be estimated. If the layers contain the same element, accurate thickness measurement or composition analysis is difficult.

When crystal structure analysis is executed for a multilayered film as a sample by using X-ray diffraction analysis, peaks overlap, and discrimination is difficult. If the sample is very thin, the peak intensity is low and hard to detect.

When a TEM (Transmission Electron Microscope) is used, the thickness of a sample can more accurately be measured because the transmission image of the sample is observed by using an electron beam. In addition, when the electron beam diffraction function of the TEM is used, the crystal structure can be evaluated at a high spatial resolution. The crystal structure of a multilayered film or a very thin film can also be evaluated. When an energy dispersive analyzer attached to the TEM is used, the composition of a sample can also be analyzed.

To execute thickness measurement or crystal structure evaluation of a sample by using the TEM, the sample needs to be so thin that an electron beam can pass through it. As is known, a sample for a TEM is prepared by using ion milling or an FIB (Focused Ion Beam) method.

Conventionally known references are D1: "Device Analysis Guidebook", edited by Japan Society for Analytical Chemistry, Maruzen Co., Ltd., Jul. 10, 1996, p. 138, p. 142, D2: "Transmission Electron Microscope", edited by Surface Science Society of Japan, Maruzen Co., Ltd., Apr. 15, 2001, pp. 33–42, D3: "Japanese Patent Laid-Open No. 5-231997", and D4: "Japanese Patent Laid-Open No. 10-19751".

SUMMARY OF THE INVENTION

However, when a sample is formed into a thin film by using ion milling or an FIB method to prepare a thin film sample that can be measured by a TEM, sample control is difficult. Labor and time are required to do it, or sample control is sometimes impossible.

The sample measurement method is a sample measurement method by an electron microscope, comprising a film formation step of forming a sample on a projection on a major surface of a substrate, an electron beam irradiation step of irradiating the sample with an electron beam from a side of the projection, and a measurement step of detecting an electron beam which is generated or reflected from or has passed through the sample irradiated with the electron beam.

In this case, since the sample is formed on the projection on the major surface of the substrate, the sample on the projection can be formed as a thin film. For this reason, sample measurement can be executed only by irradiating the sample from a side of the projection without forming a thin film by ion milling or an FIB method as a sample to be measured.

In this sample measurement method, the projection is preferably formed on the major surface by one of ion beam assisted chemical vapor deposition and electron beam assisted chemical vapor deposition.

Focused ion beam assisted CVD (Chemical Vapor Deposition) or electron beam assisted CVD is a technique for forming a three-dimensional microstructure such as the projection by the following method. A deposition gas is supplied to the major surface of the substrate on which the projection is to be formed. Simultaneously, scanning by a focused ion beam or electron beam is executed in the deposition gas. Accordingly, deposition films are sequentially formed in the region irradiated with the focused ion beam or electron beam so that the projection is formed.

Since the projection is formed by ion beam assisted CVD (or electron beam assisted CVD), the size of the projection can be adjusted by changing the scanning region of the focused ion beam (or electron beam).

In this sample measurement method, the sample may be a multilayered film formed by forming a plurality of films on a surface of the projection sequentially from a side of the projection.

When the sample is a multilayered film, preferably, in the film formation step, after the sample is formed, portions of the sample sticking outside two opposing side surfaces of the projection, which are located sequentially in a direction of irradiation of the electron beam, are removed, and in the electron beam irradiation step, the sample whose portions sticking outside the two side surfaces of the sample are removed is irradiated with the electron beam.

Accordingly, the overlap of the multiple layers of the sample outside the opposing side surfaces of the projection is removed, and the multilayered structure is exposed to the side surfaces of the sample. For this reason, the contrast of the observation image obtained by the electron microscope can be increased for each layer.

In this sample measurement method, preferably, a distance from an interface between the projection and the sample to the major surface is not less than 0.5 µm, and a length of the projection in a direction of irradiation of the electron beam on the interface is 0.2 to 1 µm.

In this sample measurement method, the electron microscope can be a transmission electron microscope, and in the measurement step, the electron beam which has passed through the sample can be detected.

The measurement sample base material is a measurement sample base material to form a sample to be measured by using an electron microscope, characterized by comprising a substrate having a major surface, and a projection which is formed on the major surface and on which the sample is to be formed.

In this case, since the measurement sample is formed on the projection, a thin film sample can easily be prepared by using the measurement sample base material.

In this measurement sample base material, the projection is preferably formed on the major surface by one of ion beam assisted chemical vapor deposition and electron beam assisted chemical vapor deposition. In this case, the size of the projection can be adjusted by changing the scanning region of the focused ion beam (or electron beam).

In this measurement sample base material, preferably, a distance from an end face of the projection on an opposite side of the major surface to the major surface is not less than 0.5 μm, and a thickness (D) of the projection is 0.2 to 1 μm in forming a sample which can easily be measured by an electron microscope. The thickness (D) indicates the distance between a set of opposing sides included in the end faces of the projection on the opposite side to the substrate major surface.

In this measurement sample base material, the electron microscope can be a transmission electron microscope.

In addition, the sample to be measured by the electron microscope can easily be prepared, and the sample can easily be measured.

BRIEF DESCRIPTION OF THE DRAWINGS

FIG. 8 shows the electron micrographs of a sample, (a) is a transmission electron micrograph of a sample, and (b) is an electron micrograph of an electron beam diffraction image at a position A in (a);

FIG. 9 shows enlarged sectional views of a sample, (a) is an enlarged sectional view showing a sample S which is cut along a plane almost perpendicular to side surfaces 13b and 13c of a projection 13 located along the direction of incidence of an electron beam E1, and (b) is an enlarged sectional view showing the sample S which is cut along a plane almost parallel to an end face 11a at the position of a line IXb—IXb in (a);

DESCRIPTION OF THE PREFERRED EMBODIMENTS

Figure 1:
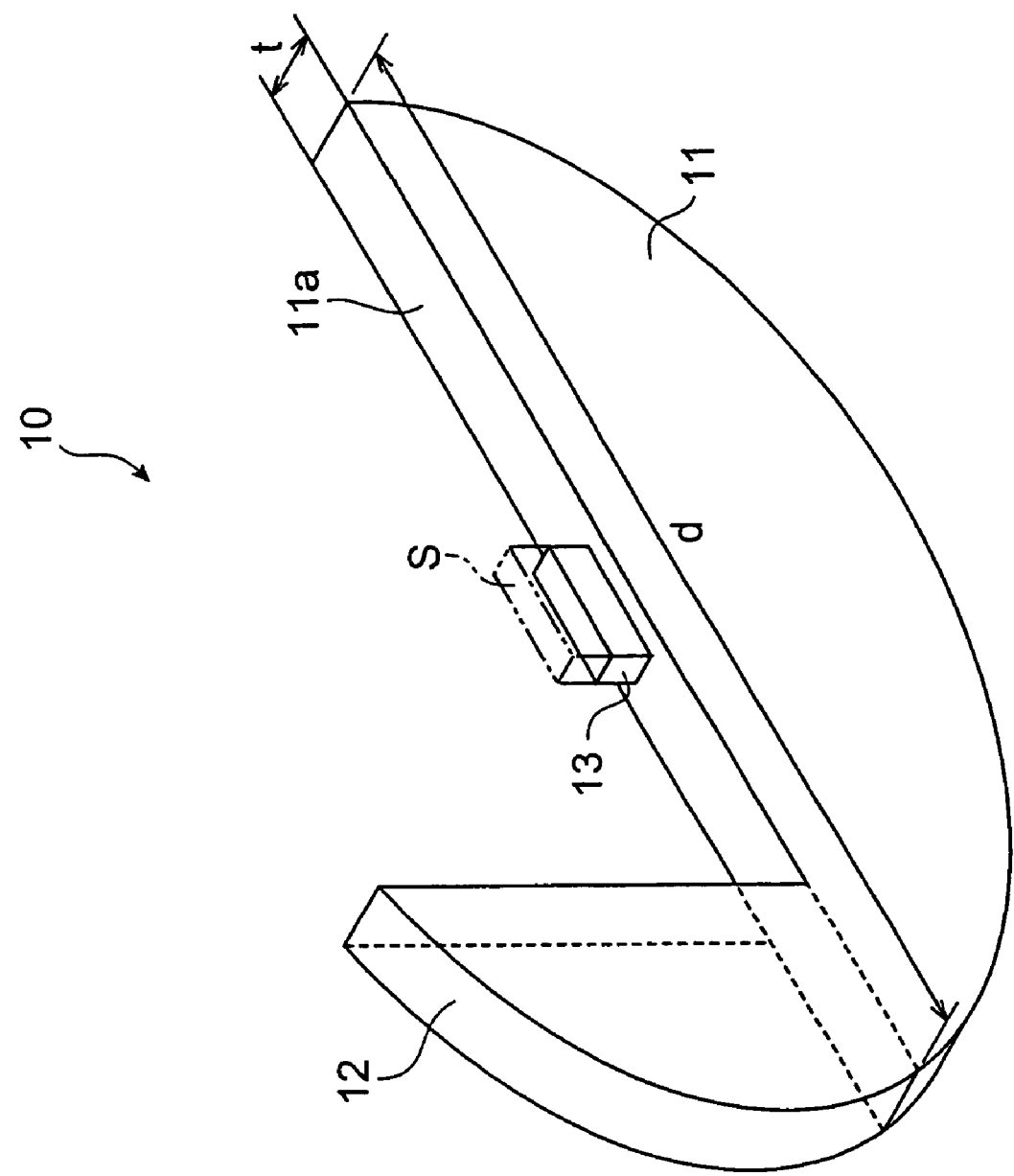
FIG. 1 is a perspective view showing the structure of a measurement sample base material according to an embodiment of the present invention.

The preferred embodiments of the present invention will be described below with reference to the accompanying drawings. In the following description, the same reference numerals denote the same elements, and a repetitive description will be omitted. Dimension ratios in the drawings do not always coincide with those in the description.

(First Embodiment)

FIG. 1 is a perspective view schematically showing the structure of a measurement sample base material 10 according to the first embodiment. This embodiment is related to a TEM (Transmission Electron Microscope).

The measurement sample base material 10 is a base material on which a sample S to be measured by a TEM is formed. The measurement sample base material 10 is a semicircular plate and has a substrate 11 made of, e.g., Cu, Be, or Mo.

A thickness t of the substrate 11 is, e.g., about 30 to 40 μm. A diameter d is, e.g., about 3 mm. A grip portion 12 and a projection 13 are formed on an end face (major surface) 11a of the substrate 11.

The grip portion 12 is formed on one end portion side of the end face 11a. The grip portion 12 has, e.g., a sector shape. The grip portion 12 is integrated with the substrate 11 by using the same material as the substrate 11. The diameter d of the substrate 11 is preferably 2.3 to 3.05 mm, which is the standard size of a sample base for a TEM. Accordingly, the substrate 11 becomes more versatile.

Figure 2:
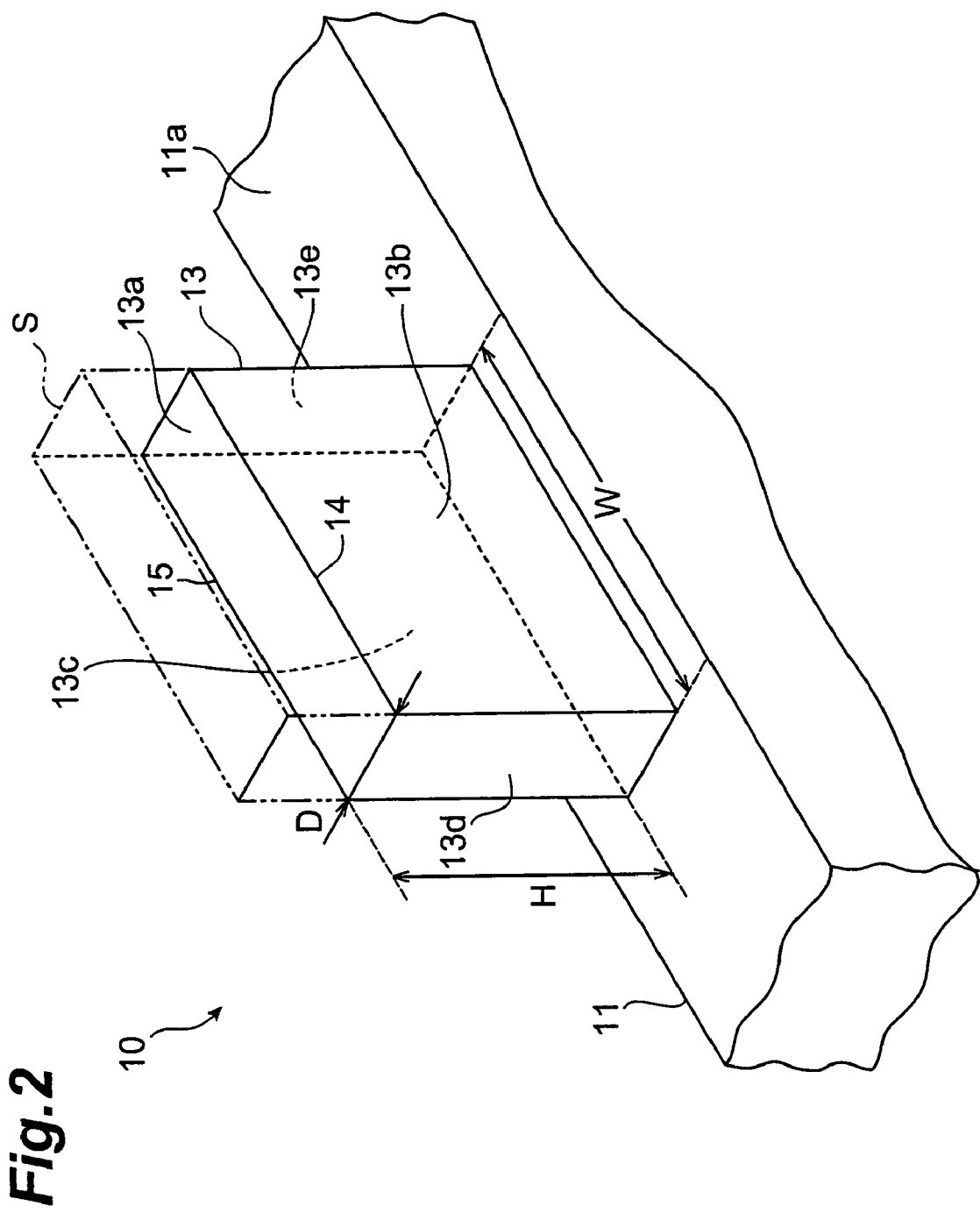
FIG. 2 is an enlarged perspective view of the projection shown in FIG. 1.

FIG. 2 is an enlarged perspective view of the projection 11.

The projection 13 is formed on the end face 11a of the measurement sample base material 10 in a region where the grip portion 12 is not formed. The projection 13 has a plate shape and is formed as a projection extending in the longitudinal direction of the end face 11a.

The projection 13 need not always be a projection. A height H, which is the distance from the end face 11a of the substrate 11 to an end face 13a of the projection 13 on the opposite side of the substrate 11, is, e.g., 0.5 μm or more. A thickness D of the projection 13 is, e.g., 0.2 to 1 μm. The thickness D of the projection 13 indicates the distance between a set of opposing sides 14 and 15 of the end face 13a.

A width W of the projection 13, which is the distance between two opposing side surfaces 13d and 13e, is, e.g., 0.01 to 20 μm.

As long as the thickness D of the projection 13 is 0.2 to 1 μm, the sectional shape obtained by cutting the projection 13 along a plane almost perpendicular to a side surface 13b (or side surface 13c) is not particularly limited. The sectional shape may be, e.g., either a tapered shape in which the distance between the side surface 13b and the side surface 13c is longer on the side of the substrate 11 than on the side of the end face 13a or an inverted tapered shape in which the distance between the side surface 13b and the side surface 13c is shorter on the side of the substrate 11 than on the side of the end face 13a.

The sample S is formed on the end face 13a of the projection 13. Since the sample S is to be formed on the projection 13, the projection 13 is preferably made of the same material as the substrate 11 or a material which is thermally stable and not so highly reactive to the sample S for appropriate measurement of the sample S. Examples of the material of the projection 13 are W, Pt, and C.

The projection 13 is formed by ion beam assisted CVD (Chemical Vapor Deposition) in which a three-dimensional microstructure is formed by using an FIB (Focused Ion Beam) apparatus, or a method called FIB-CVD.

Figure 3:
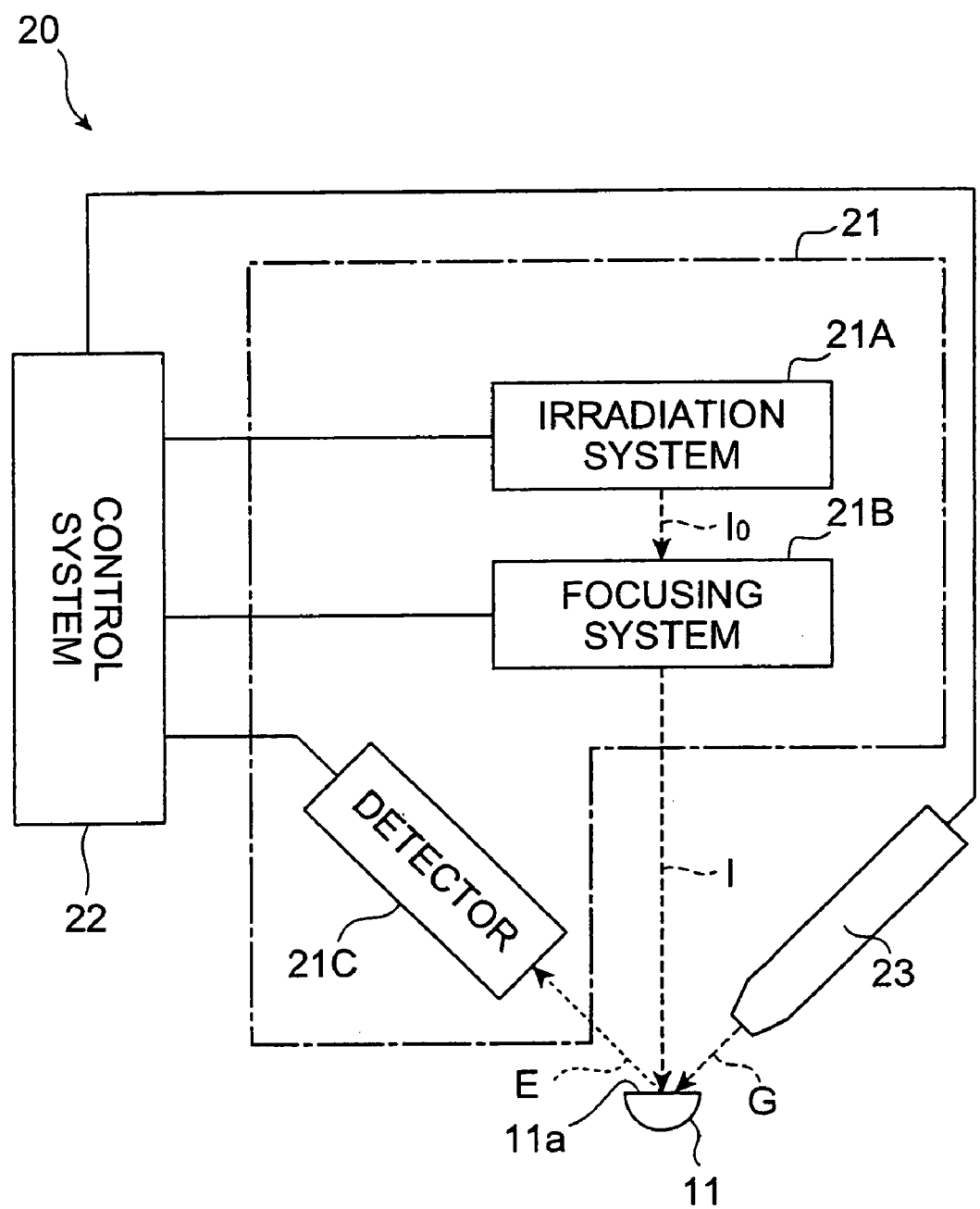
FIG. 3 is a schematic view showing the arrangement of an FIB apparatus.

FIG. 3 is a schematic view showing the arrangement of an FIB apparatus 20 to be used for ion beam assisted CVD.

The FIB apparatus 20 has an ion optical system 21, a control system 22, and a nozzle 23 which ejects a deposition gas. The ion optical system 21 includes an irradiation system 21A, focusing system 21B, and detector 21C.

The irradiation system 21A has an ion source and generates an ion beam $I_0$. As ions, for example, Ga ions, Cs ions, or Au ions are used.

The focusing system 21B includes a condenser lens and an objective lens. The focusing system 21B changes the ion beam $I_0$ generated by the irradiation system 21A to a focused ion beam I and irradiates the end face 11a of the substrate 11 with it. The focusing system 21B has a function of changing the direction of the focused ion beam I so that the focused ion beam I can scan the end face 11a.

The detector 21C detects secondary electrons E emitted from a region on the end face 11a, which is irradiated with the focused ion beam I, and outputs an image signal.

The control system 22 controls various functions of the FIB apparatus 20. The control system 22 has a signal processing function of converting a signal obtained by the detector 21C into an image and displaying it on a monitor, a function of controlling the deposition gas supply amount, and a function of changing the size of the focused ion beam I and switching the observation image magnification.

The ejection port of the nozzle 23 is directed to the end face 11a. The nozzle 23 supplies a deposition gas G as the material of the projection 13 onto the end face 11a.

The FIB apparatus 20 has constituent elements which a generally known FIB apparatus should have in addition to those described above. However, for the descriptive convenience of the embodiment of the present invention, an illustration and description of the constituent elements will be omitted. In FIG. 3, the substrate 11 as a process target in forming the projection 13 is illustrated in a schematic form, and the grip portion 12 is not illustrated.

Figure 4:
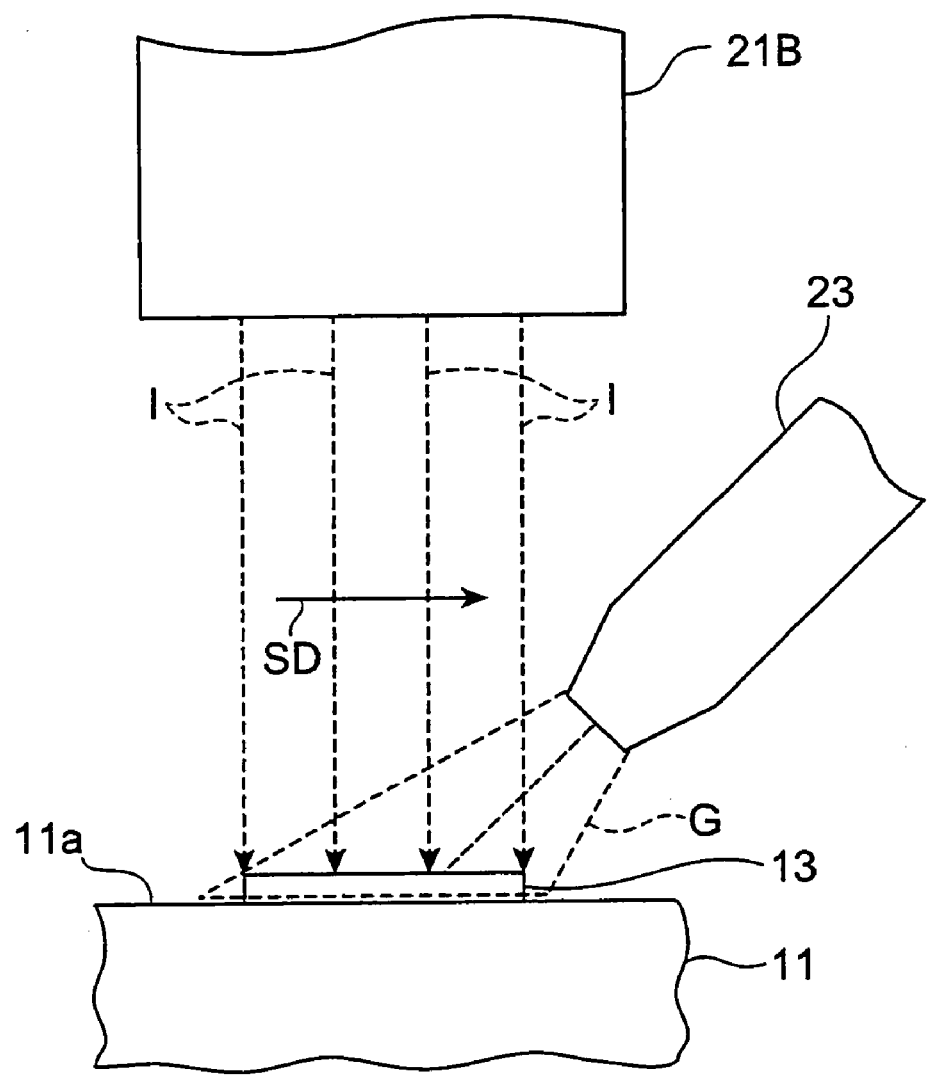
FIG. 4 is a view showing a projection formation step.

FIG. 4 is a view showing the step of forming the projection 13.

To form the projection 13, first, the deposition gas G is ejected from the nozzle 23 to the end face 11a of the substrate 11. In the ion optical system 21, the irradiation system 21A outputs the ion beam $I_0$ which enters the focusing system 21B. The focusing system 21B changes the ion beam $I_0$ to the focused ion beam I and irradiates the end face 11a with it.

Secondary electrons which are emitted from the substrate 11 when the focused ion beam I collides against the substrate 11 on the end face 11a or the decomposed components of the deposition gas G by the focused ion beam I reach the end face 11a.

When the focused ion beam I scans the end face 11a of the substrate 11 (scan direction SD), a deposition film is formed in the region irradiated with the focused ion beam I. When scanning of the focused ion beam I is repeated in the region where the projection 13 is to be formed, deposition films are sequentially formed so that the projection 13 is formed.

The higher the concentration of the deposition gas G in the region where the projection 13 should be formed is, and the larger the secondary electron generation amount on the end face 11a is, the higher the formation efficiently of the projection 13 becomes. The secondary electron generation amount increases in accordance with the ion dose. However, when the ion dose is high, the etching rate of the substrate 11 becomes high, and accordingly, the formation efficiency of the projection 13 decreases.

For this reason, the projection 13 is preferably formed by using an optimum ion dose in accordance with the supplied deposition gas amount or ion irradiation region. The deposition gas amount and ion dose are controlled by the control system 22.

Figure 5:
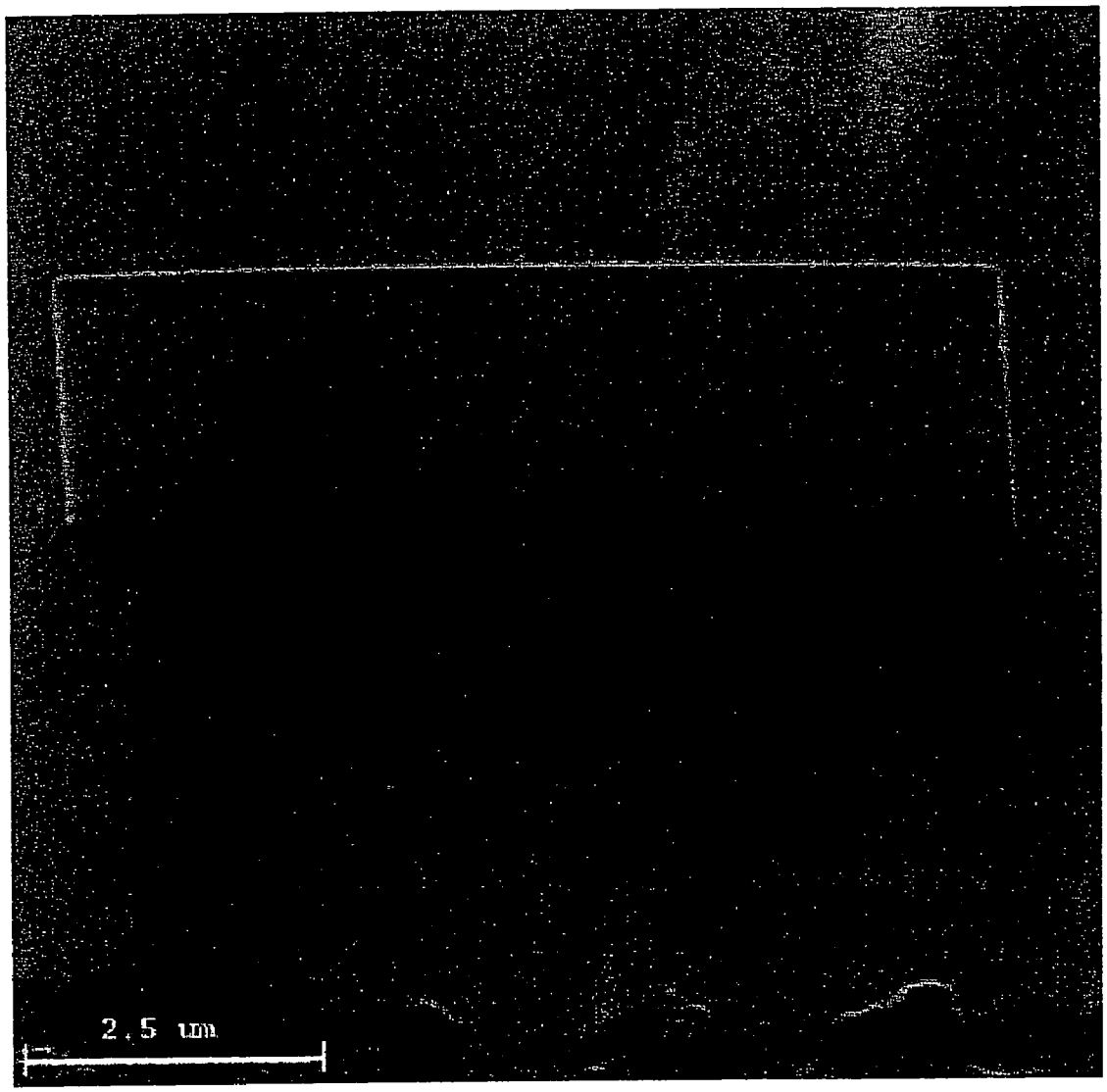
FIG. 5 is an electron micrograph of a projection formed by the step shown in FIG. 3.

FIG. 5 is an electron micrograph of the projection 13 on the substrate 11, which is formed by the above-described method.

The height H of the projection 13 shown in FIG. 5 is about 2.7 μm, the width W is about 7.7 μm, and the thickness D is about 0.26 μm. The projection 13 is made of carbon (C).

Figure 6:
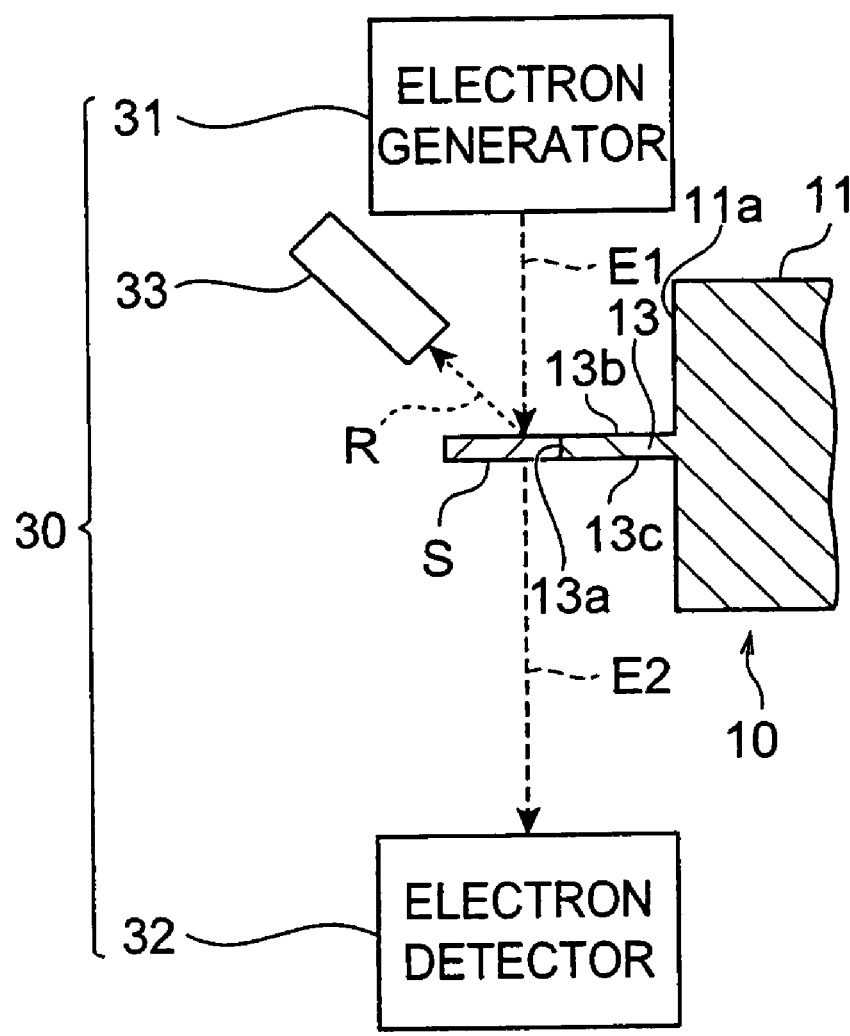
FIG. 6 is a schematic view showing the arrangement of a TEM.

FIG. 6 is a schematic view showing a TEM 30 to observe the sample S formed on the measurement sample base material 10.

A sample measurement method according to this embodiment by the TEM 30 using the measurement sample base material 10 will be described with reference to FIG. 6. First, the sample S is formed on the end face 13a of the projection 13 of the measurement sample base material 10. Then, the measurement sample base material 10 is arranged in the TEM 30. As the sample S, a sample made of a desired material is formed by, e.g., sputtering. The sample S can be either a single-layered film or a multilayered film. For the sake of simplicity, a description will be made here for a single-layered film.

The TEM 30 comprises an electron generator 31, electron detector 32, and EDS (Energy Dispersive Spectroscopy) analyzer 33. The TEM 30 also has various kinds of observation/analysis functions (e.g., a scanning electron microscope function). However, an illustration and description of the functions will be omitted for the descriptive convenience of this embodiment.

The electron generator 31 includes an electron gun and convergent lens and outputs an electron beam. The electron detector 32 includes an objective lens, projecting lens, fluorescent screen, and image sensing device. The electron detector 32 has an electron beam diffraction function which is normally attached to a TEM. The EDS analyzer 33 detects an X-ray R emitted from the sample S and analyzes its energy. It is an EDS analyzer normally attached to a TEM.

The measurement sample base material 10 is set between the electron generator 31 and the electron detector 32 such that an electron beam E1 output from the electron generator 31 becomes incident on the sample S from a side of the projection 13 (i.e., a direction almost perpendicular to the side surfaces 13b and 13c).

In the state in which the measurement sample base material 10 is thus set, the electron generator 31 outputs the electron beam E1 and irradiates the sample S with it from a side of the projection 13. Of the electron beam E1, an electron beam component E2 that has passed through the sample S is detected by the electron detector 32. More specifically, in the electron detector 32, an image is formed on the fluorescent screen on the basis of the electron beam E2 that has entered the electron detector 32. The thickness of each layer can be measured on the basis of the image.

In addition, when the electron beam diffraction function of the electron detector 32 is used, an electron beam diffraction image of the sample S can be obtained. Hence, the crystal structure of the sample S can be evaluated. The X-ray R emitted from the sample S in accordance with the electron beam E1 that has become incident on the sample S is detected by the EDS analyzer 33. Accordingly, the composition of the sample S is analyzed.

As described above, when various kinds of functions attached to the TEM 30 are used, the thickness of the sample S can more accurately be measured. In addition, crystal structure evaluation and composition analysis are possible. In the above-described sample measurement method, the electron beam E2 that has passed through the sample S is detected. When the TEM 30 has, e.g., a scanning electron microscope function, an electron beam generated and reflected from the sample S may be detected.

Figure 7:
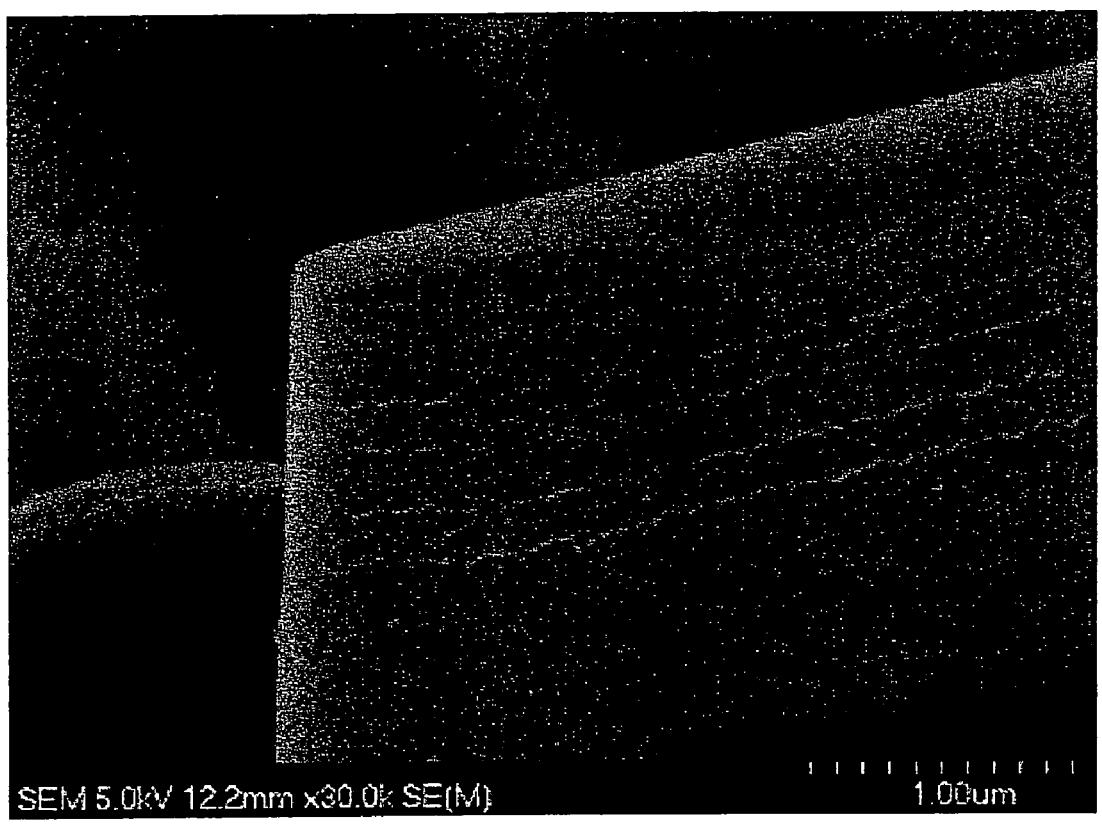
FIG. 7 is an electron micrograph of a projection on which a sample is formed.

FIG. 7 is an electron micrograph of the projection 13 when the sample S is formed on the measurement sample base material 10 shown in FIG. 5. The sample S shown in FIG. 7 includes a single-layered structure.

In FIG. 8, (a) shows a transmission electron micrograph of a ZnS film which is formed as the sample S on the projection 13 made of carbon and having the thickness D of 0.25 µm.

In FIG. 8, (b) shows an electron micrograph of the sample. A transmission image of the sample S on the projection 13 is obtained from (a) of FIG. 8. An appropriate interface contrast is obtained between the sample S and the projection 13 so that the thickness of the sample S can be measured.

In FIG. 8, (b) shows an electron beam diffraction image at a position A in (a) of FIG. 8.

As is apparent from (b) of FIG. 8, an electron beam diffraction image of the sample S can also be acquired, and the crystal structure can be evaluated.

As described above, the sample S is formed on the projection 13 for which the thickness D in the direction of incidence of the electron beam E1 is, e.g., 0.2 to 1 µm. That is, the sample S is a thin film which can be measured by the TEM 30.

Hence, when the sample S is formed on the measurement sample base material 10, and the measurement sample base material 10 is set in the TEM 30, the sample S can be measured. The sample S can be measured without executing the step of preparing a sample to be measured in advance and forming a thin film of the sample for the TEM 30 by using ion milling or the FIB method, unlike the prior art. In other words, by the measurement method using the measurement sample base material 10, a sample for the TEM 30 can more easily be prepared than the prior art, and sample measurement can easily be executed.

The thickness is measured after obtaining a transmission image of the sample S by the TEM 30. For this reason, the thickness can more accurately be measured than fluorescent X-ray analysis in which the thickness is calculated after data is analyzed by using, e.g., the density of the reference value. Furthermore, when both of the electron beam diffraction function and EDS analyzer 33, which are attached to the TEM 30, are used, crystal structure analysis and composition analysis of the sample can also be executed.

The height H as the distance from the interface between the projection 13 and sample S to the end face 11a is 0.5 µm or more. The sample S is held at a position separated from the end face 11a by 0.5 µm or more. For these reasons, when the measurement sample base material 10 is set in the TEM 30, the sample S can easily be irradiated with the electron beam E1 so that the sample S can easily be measured. In the above description, the sample S is a single-layered film. However, as described above, the sample S may be a multilayered film formed by forming a plurality of films on the surface of the projection 13 sequentially from the side of it.

FIG. 9 shows an enlarged sectional view, and (a) of FIG. 9 shows the sample S which is cut along a plane almost perpendicular to the side surfaces 13b and 13c of the projection 13 located along the direction of incidence of the electron beam E1. As is apparent from (a) of FIG. 9, the sample S is a multilayered film formed by forming, e.g., an $Al_2O_3$ film $S_1$, $SiO_2$ film $S_2$, and $Al_2O_3$ film $S_3$ on the projection 13 sequentially for the side of it. Even when the sample S is such a multilayered film, the thickness of each layer can more accurately be measured than fluorescent X-ray analysis because the thickness is measured from a transmission image.

In FIG. 9, (b) shows an enlarged sectional view showing the sample S which is cut along a plane almost parallel to the end face 11a at the position of a line IXb—IXb in (a) of FIG. 9.

A case will be described, in which the sample S is a multilayered film, as shown in (a) and (b) of FIG. 9, and has portions sticking outside the side surfaces 13b and 13c of the projection 13.

The portions sticking outside the side surfaces 13b and 13c indicate a portion of the sample S on the opposite side of the side surface 13c when viewed from a plane α including the side surface 13b and a portion of the sample S on the opposite side of the side surface 13b when viewed from a plane β including the side surface 13c. For the descriptive convenience, the sample S outside the plane α or β will also be referred to as a portion sticking to the plane α or β.

When portions of the sample S stick outside the side surfaces 13b and 13c of the projection 13, the following fabrication is preferably executed.

The portions sticking to the planes α and β (i.e., regions of the sample S, which project from the projection 13) are removed by the FIB method or ion milling. Then, the sample S whose portions sticking to the planes α and β are removed is preferably irradiated with the electron beam E1 to execute measurement. In this sticking portion removing method, the removal amount is very small. Hence, the operating efficiency is much higher than a normal method of fabricating a section observation sample from a substrate.

Accordingly, the overlap of layers of the sample S outside the side surfaces 13b and 13c is removed, and the multilayered structure is exposed. Since the contrast of the transmission image by the TEM 30 increases, the thickness of each layer can more accurately be measured.

In this case, the sample S is removed by the FIB method or ion milling. Since the region to be removed is small, the time necessary for fabrication can be shortened as compared to the conventional method of forming a thin film as a sample for the TEM 30.

Referring to FIG. 1, one projection 13 is formed on the end face 11a. A plurality of projections 13 may be formed on the end face 11a of the substrate 11. The measurement sample base material 10 has one grip portion 12. The grip portions may be formed at two ends of the end face 11a in the longitudinal direction. The grip portion need not always be formed at all.

The projection 13 is formed by ion beam assisted CVD using the focused ion beam I. It is more preferably to use electron beam assisted CVD using an electron beam in place of the focused ion beam I. In this case, since an electron beam is used, no ions of the focused ion beam I are contained in the projection 13. Accordingly, the projection 13 having high heat resistance can be formed.

(Second Embodiment)

Figure 10:
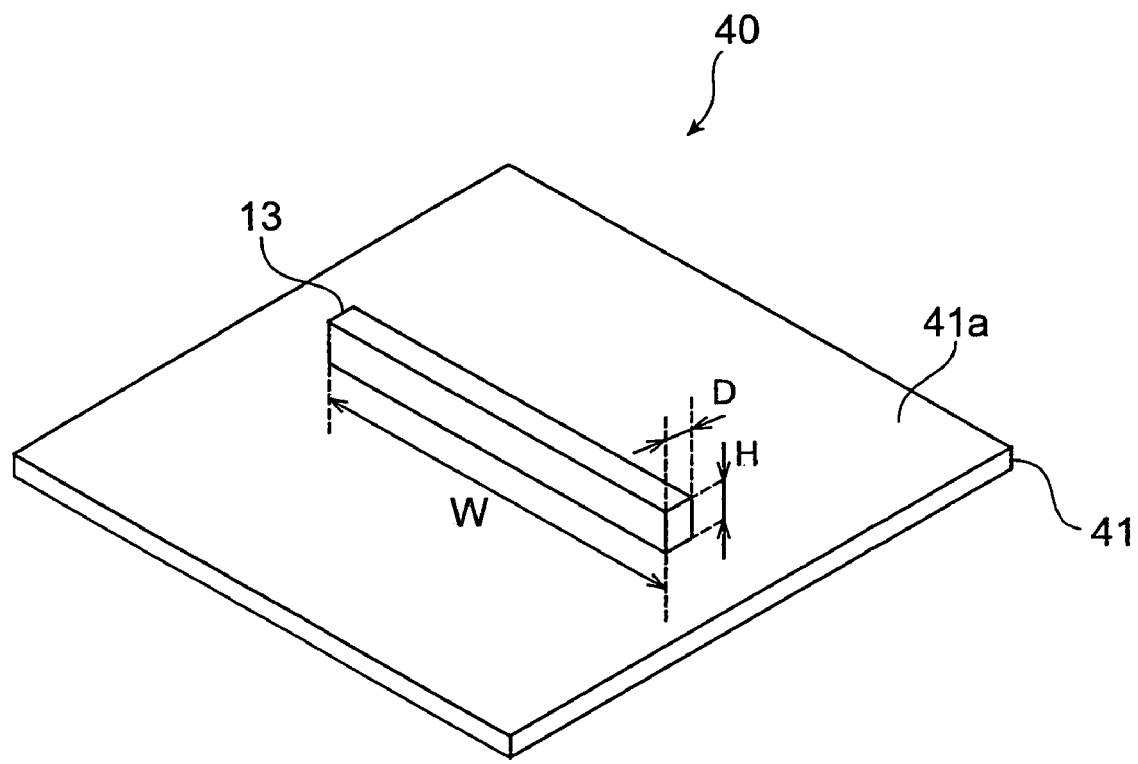
FIG. 10 is a perspective view schematically showing the structure of a measurement sample base material according to another embodiment of the present invention.

FIG. 10 is a perspective view showing the schematic structure of a measurement sample base material according to the second embodiment.

In a measurement sample base material 40, a substrate 41 is different from the substrate 11 of the first embodiment in that the substrate 41 has not a semicircular plate shape but an almost rectangular plate shape. The substrate 41 is, e.g., an Si substrate having a size of about 2 mm square. A projection 13 is formed on a surface (major surface) 41a of the substrate 41. A width W of the projection 13 is, e.g., 100 µm but may be the same as in the first embodiment. A thickness D and height H are the same as in the first embodiment.

Figure 11:
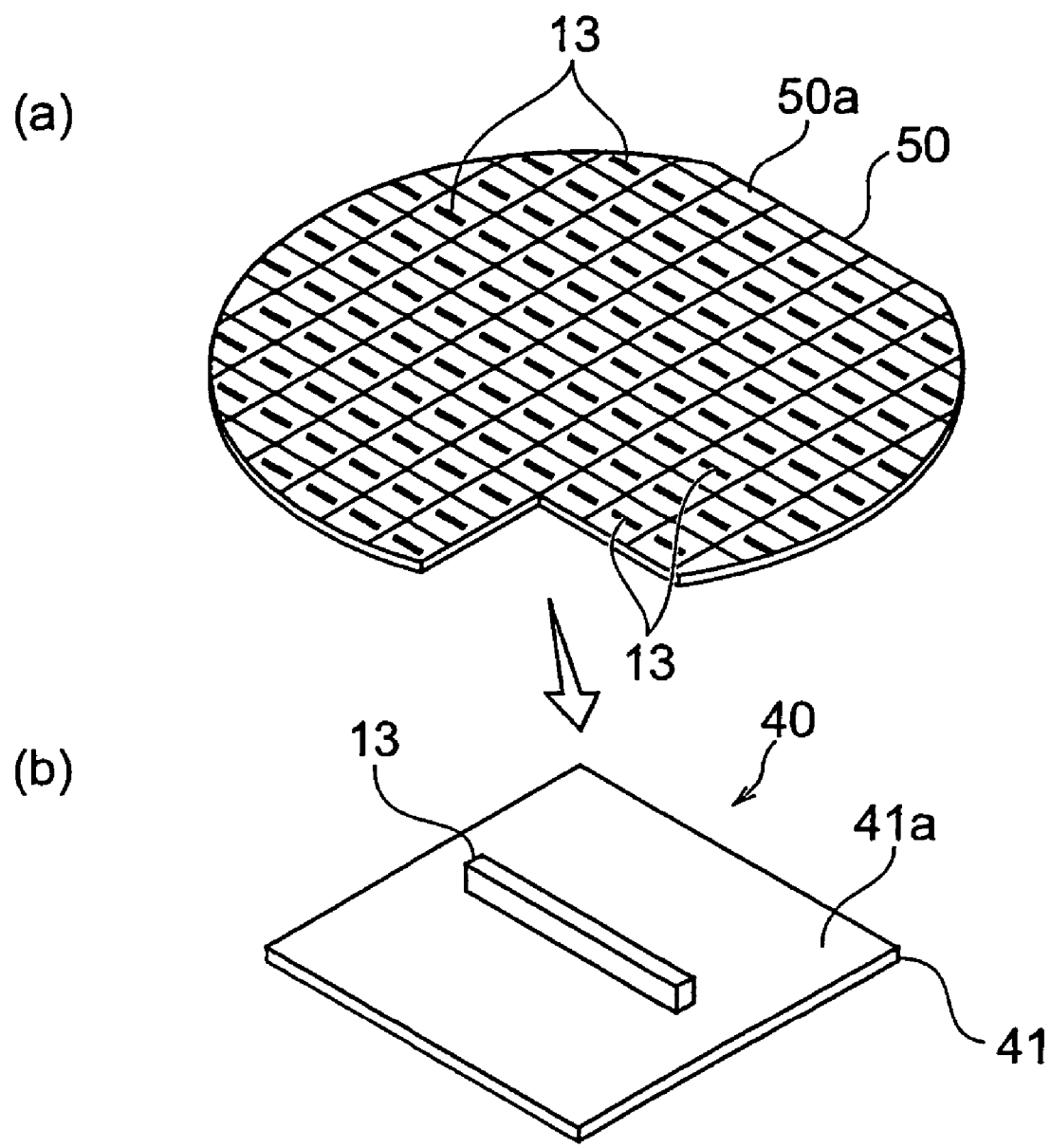
FIG. 11 shows the step of preparing the measurement sample base material shown in FIG. 10, (a) is a perspective view showing a wafer so as to explain the step of preparing the measurement sample base material shown in FIG. 10, and (b) is a perspective view showing a base material so as to explain the step of preparing the measurement sample base material shown in FIG. 10.

FIG. 11 shows the step of preparing the measurement sample base material shown in FIG. 10. In FIG. 11, (a) shows a perspective view of a wafer. In FIG. 11, (b) shows a perspective view of the base material.

To prepare the measurement sample base material 40, first, a plurality of projections 13 are formed on a surface 50a of an Si wafer 50 by ion beam assisted CVD. The Si wafer 50 is divided into pieces of about 2 mm square each including the projection 13, thereby preparing a plurality of measurement sample base materials 40. The projections 13 are more preferably formed by electron beam assisted CVD, as in the first embodiment.

Figure 12:
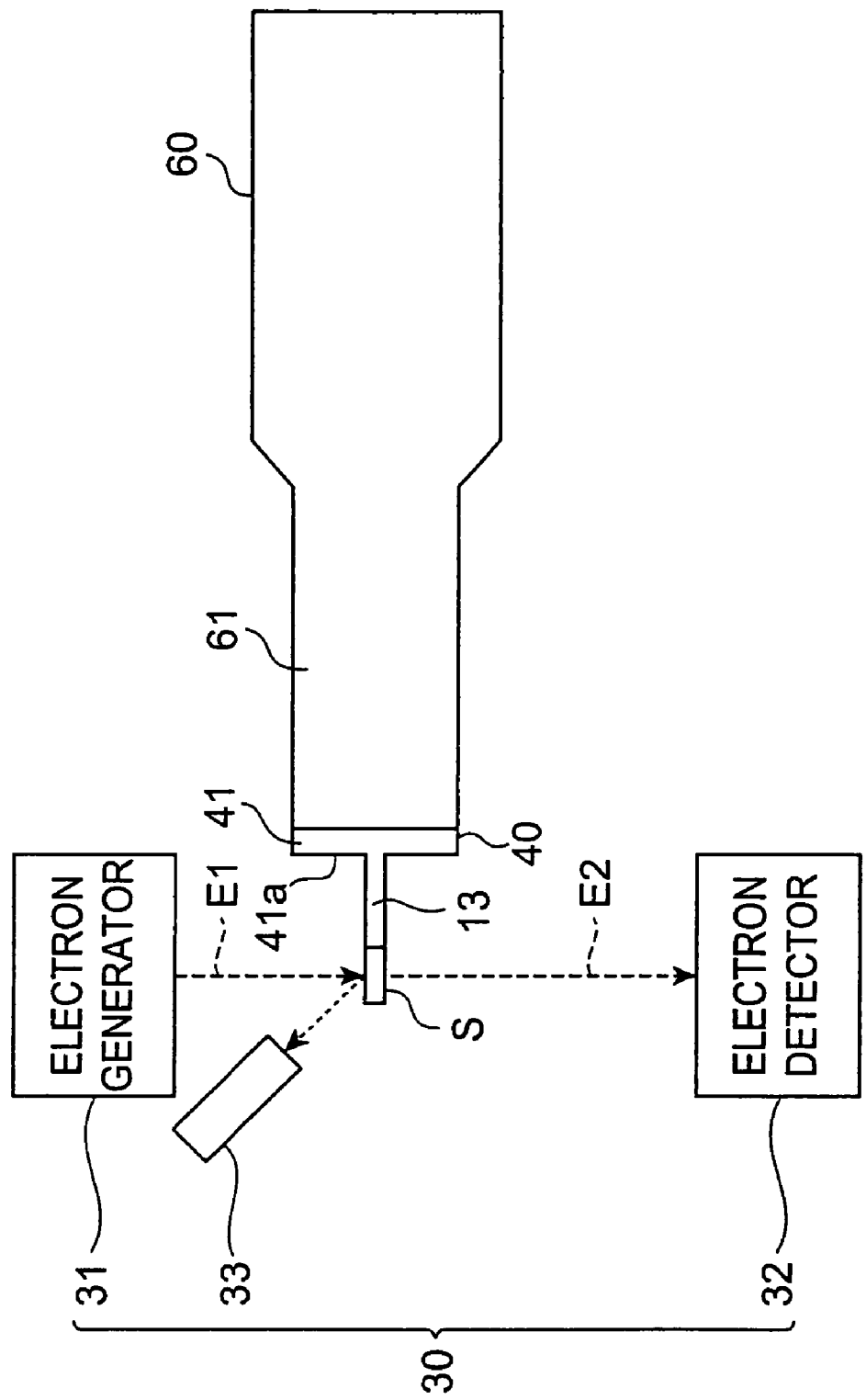
FIG. 12 is a schematic view showing a method of measuring a sample using the measurement sample base material shown in FIG. 10.

FIG. 12 is a schematic view showing a method of measuring a sample S by a TEM 30 using the measurement sample base material 40.

To measure the sample S by using the measurement sample base material 40, first, the sample S is formed on the projection 13 of the measurement sample base material 40. Then, the measurement sample base material 40 is fixed on a distal end portion 61 of a support 60. The sample S is irradiated with an electron beam E1 from a side of the projection 13, and an electron beam E2 that has passed through the sample S is detected, as in the first embodiment. The sample S can be either a single-layered film or a multilayered film, as in the first embodiment.

The projections 13 are formed on the Si wafer 50 in advance. After that, the Si wafer is divided into the substrates 41. Hence, the measurement sample base materials 40 can easily be mass-produced.

In this embodiment, the measurement sample base material 40 is prepared, and then, the sample S is formed on the projection 13. Instead, the sample S may be formed on each of the plurality of projections 13 formed on the Si wafer 50. After that, the Si wafer is divided into the measurement sample base materials 40. In this case, when the sample S on each measurement sample base material 40 is measured, the thickness distribution of the sample S in the plane of the Si wafer 50 can be obtained.

In the above description, the substrate 41 of the measurement sample base material 40 is an Si substrate having a size of about 2 mm square. If the substrate can be set in the TEM 30, the size is not limited to 2 mm square. The substrate need not always be an Si substrate.

The preferred embodiments of the present invention have been described above. However, the present invention is not limited to the first and second embodiments. For example, an sample formed on the projection 13 by ion beam assisted CVD or electron beam assisted CVD is measured by the TEM. The sample S formed on the projection 13 formed by another method on the major surface of the substrate 11 or 41 may be measured.

As another method of forming the projection 13, ion milling or the FIB method can be used to fabricate the substrate 11 or 41. However, ion beam assisted CVD or electron beam assisted CVD is preferable because the size of the projection 13 can more accurately be adjusted.

The substrates 11 and 41 are a semicircular plate and a plate, respectively. However, the shape is not particularly limited as long as the substrate can be set in the TEM. However, a substrate having a general size for TEM is suitable because of its versatility.

In the projection 13, the sample S is formed on the end face 13a on the opposite side of the substrate 11. However, the position is not limited to this. As far as the length of the sample S in the direction of irradiation of the electron beam E1 is a length observable by the TEM, the sample S only needs to be formed on the projection 13.

The projection 13 has a plate shape. However, the shape is not limited to this. However, it is suitable that the length (thickness D in FIG. 2) in the electron beam irradiation direction on the interface between the sample S and the projection 13 is 0.2 to 1 µm, and the distance from the interface between the sample S and the projection 13 to the end face 11a (or end face 41a) is 0.5 µm or more.

In the first and second embodiments, the sample is measured by using the TEM. The sample measurement method and measurement sample base material according to the present invention can also be applied to another electron microscope such as an SEM (Scanning Electron Microscope).

For example, when a sample is to be measured by an SEM, the sample S to be measured is formed on the projection 13 of the measurement sample base material 10, as in the case of TEM. The measurement sample base material 10 is set in the SEM such that the sample S is irradiated with an electron beam from a direction almost perpendicular to the side surfaces 13b and 13c of the projection 13.

Subsequently, the sample S formed on the projection 13 is irradiated with an electron beam. Secondary electrons or reflected electrons generated from the sample S irradiated with the electron beam are detected.

When the sample S is a multilayered film, and the sample S is to be measured by using an SEM, a portion (a portion sticking to the plane α or β in FIG. 9) outside the side surface 13b or 13c is removed, as in the case of TEM. In the SEM, it is only necessary to obtain contrast of secondary electrons or reflected electrons. Hence, only one side portion is removed. In other words, a portion sticking to one of the plane α including the side surface 13b and the plane β including the side surface 13c is removed.

What is claimed is:

1. A sample measurement method by an electron microscope, comprising:
    a film formation step of forming a sample on a projection on a major surface of a substrate;
    an electron beam irradiation step of irradiating the sample with an electron beam from a side of the projection; and
    a measurement step of detecting an electron beam which is generated or reflected from or has passed through the sample irradiated with the electron beam.

2. A method according to claim 1, characterized in that the projection is formed on the major surface by one of ion beam assisted chemical vapor deposition and electron beam assisted chemical vapor deposition.

3. A method according to claim 1, characterized in that the sample is a multilayered film formed by forming a plurality of films on a surface of the projection sequentially from a side of the projection.

4. A method according to claim 3, characterized in that in the film formation step, after the sample is formed, portions of the sample sticking outside two opposing side surfaces of the projection, which are located sequentially in a direction of irradiation of the electron beam, are removed, and in the electron beam irradiation step, the sample whose portions sticking outside the two side surfaces of the sample are removed is irradiated with the electron beam.

5. A method according to claim 1, characterized in that a distance from an interface between the projection and the sample to the major surface is not less than 0.5 µm, and a length of the projection in a direction of irradiation of the electron beam on the interface is 0.2 to 1 µm.

6. A method according to claim 1, characterized in that the electron microscope is a transmission electron microscope, and in the measurement step, the electron beam which has passed through the sample is detected.

7. A method according to claim 2, characterized in that the sample is a multilayered film formed by forming a plurality of films on a surface of the projection sequentially from a side of the projection.

8. A measurement sample base material to form a sample to be measured by using an electron microscope, comprising:

a substrate having a major surface; and a projection that is formed on the major surface and on which the sample is to be formed, the projection having a height dimension extending in a direction perpendicular to the major surface, and a width dimension and a thickness dimension extending in directions parallel to the major surface and perpendicular to each other, and the width dimension being less than a width of the major surface, and greater than the height dimension and the thickness dimension.

9. A base material according to claim 8, characterized in that said projection is formed on the major surface by one of ion beam assisted chemical vapor deposition and electron beam assisted chemical vapor deposition.

10. A base material according to claim 8, characterized in that the height dimension is not less than 0.5 µm, and the thickness dimension is 0.2 to 1 µm.

11. A base material according to claim 8, characterized in that the electron microscope is a transmission electron microscope.

12. A base material according to claim 9, characterized in that the height dimension is not less than 0.5 µm, and the thickness dimension is 0.2 to 1 µm.

* * * * *